United States Patent [19]

Baird et al.

[11] Patent Number: 5,126,461
[45] Date of Patent: Jun. 30, 1992

[54] PROCESS FOR OPENING CYCLOPROPANE RINGS

[75] Inventors: Mark S. Baird, Newcastle-upon-Tyne; Ian Bruce, Oxford, both of United Kingdom

[73] Assignee: Shell Research Limited, United Kingdom

[21] Appl. No.: 612,667

[22] Filed: Nov. 14, 1990

[30] Foreign Application Priority Data

Nov. 16, 1989 [GB] United Kingdom ............... 8925978

[51] Int. Cl.$^5$ ................. C07D 333/08; C07D 307/36
[52] U.S. Cl. .............................. 549/80; 549/51; 549/60; 549/62; 549/66; 549/78; 549/505; 549/506; 549/497; 549/504; 549/479; 568/655; 568/656; 570/128; 570/182; 570/185; 585/476; 585/506; 546/346; 546/348; 546/288; 546/280; 546/275; 546/283; 546/284; 548/182; 548/183; 548/202; 548/213; 548/206
[58] Field of Search ............... 549/504, 479, 497, 505, 549/506, 60, 59, 62, 78, 80, 66; 570/128, 185, 182; 568/655, 656; 585/476, 500; 546/346, 348, 288, 280, 275, 283, 284; 548/187, 113, 202, 213, 206

[56] References Cited

PUBLICATIONS

Reese, C. B., "Stereochemistry of Solvolysis of Halogenocarbene Adducts of Cyclic Olefins", *J. Chem. Soc. Chem. Comm.*, 1970, pp. 1365-1366.

Meisels, G. G., et al., "Ionization and Dissociation of C$_4$H$_8$ Isomers", *J. Amer. Chem. Soc.*, vol. 92, 1970, pp. 254-258.

Alonso, Miguel E., et al., "Synthesis of Alpha-Carboxy-Gamma-Butyrolactones on Silica Surfaces", *J. Heterocyclic Chem.*, vol. 19, Mar.-Apr. 1982, pp. 369-371.

Baird, M. S. et al., "Silver-Induced Ring-Opening of Some Tri-Tetrahalogenocyclopropanes", *J. Chem. Research*, 1988, pp. 292-293.

A. Padwa, *J. Chem. Soc. Perkin I*, "Photorearrangement Studies of 3-Heteroaryl-Substituted Cyclopropanes", pp. 2671-2676 (1984).

*Primary Examiner*—Richard L. Raymond
*Assistant Examiner*—Mark W. Russell

[57] ABSTRACT

Process for ring opening compounds of the formula

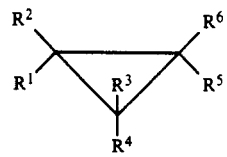

in which $R^1$ is heteroaryl or aryl, $R^2$ is a leaving group, $R^3$, $R^4$, $R^5$ and $R^6$ are independently selected from hydrogen, alkyl, aralkyl, aryl, heteroaryl and alkenyl, provided that at least one of the groups $R^3$ to $R^6$ is other than hydrogen, by breaking the bond joining the carbon atom attached to $R^3$ and the carbon atom attached to $R^6$ in organic solution using silica, giving useful diene or allyl derivatives, certain of which are novel.

8 Claims, No Drawings

PROCESS FOR OPENING CYCLOPROPANE RINGS

The present invention relates to processes in which the rings of cyclopropane derivatives having a leaving group, are cleaved to form diene compounds or allyl compounds, and to novel thiophene derivatives of dienes that can be made by the process.

It is known that cyclopropane derivatives having a leaving group substituted in the ring (1-position) can undergo ring opening at the 2→4 bond. It is known that other ring substituents affect the ease with which that reaction proceeds.

It is known that halogen substituted cyclopropane derivatives can be subjected to ring opening promoted by silver ion in the presence of methanol. Addition of silver trifluoromethanesulphonate in methanol with the dissolved cyclopropane results in precipitation of silver halide and production of an allyl methyl ether compound or mixture of compounds. Such reactions are described in, for instance, J Chem. Soc. Chem. Comm. (1970) 1365 by Reese et al, J Amer Chem. Soc. (1970) 92 256 and in J Chem. Res S. (1988) 292 by Baird et al. However the yields of such a reaction are often poor and work-up of the product not easy.

An alternative method of converting cyclopropane derivatives to allyl compounds or dienes is to heat them with quinoline. However the reactant mixture goes thick and black and a series of acid and base extractions is necessary to isolate the product (M.S. Baird (private communication)).

Alonso et al in J. Heterocyclic Chem. 19,369 (1982) describe a rearrangement of activated cyclopropanes on silica. The mechanism involves activating the cyclopropane ring via electron-withdrawing substituents and subsequent interaction with a nucleophile leading to ring opening.

Padwa et al in J. Chem. Soc. Perkins Trans. I 1984 describe a photorearrangement of 3-heteroaryl-substituted cyclopropenes. Silica gel chromatography is used as a method of purification.

In a new process according to the present invention a compound of the formula I:

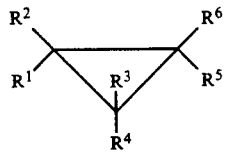

in which $R^1$ is a heteroaryl or an aryl group, $R^2$ is a leaving group, and $R^3$, $R^4$, $R^5$ and $R^6$ are independently selected from hydrogen, alkyl, aralkyl, aryl, heteroaryl and alkenyl groups, provided that at least one of the groups $R^3$ to $R^6$ is other than hydrogen, is contacted in organic solution with silica to open the ring by breaking the bond joining the carbon atom attached to $R^3$ and the carbon atom attached to $R^6$ to produce a diene or allyl product.

In the new process any heteroaryl, aryl, alkyl, aralkyl or alkenyl groups represented by any of the R groups can be substituted by substituents which do not prevent the ring opening reaction taking place or which promote the reaction. Substituents which tend to promote the reaction are electron donating substituents, such as alkoxy groups, alkyl groups, halo atoms and aryl groups.

In the compound of the formula I it is to be understood that, where appropriate, two of the groups $R^3$-$R^6$ may together represent a lower $\alpha$, $\omega$-alkylene group. Thus R groups on adjacent C atoms, for example $R^4$ and $R^5$, together represent $C_{2-6}$ alkylene or R groups on the same C atom, for example $R^3$ and $R^4$, together may represent $C_{3-7}$ $\alpha$, $\omega$-alkylene. Such alkylene groups may be substituted as described above.

$R^2$ is a leaving group, ie a group which can form an ion $(R^2)^-$. It is preferably a halogen atom, usually bromine or chlorine A halogen atom thus leaves as a halide ion.

$R^1$ is a heteroaryl group, for instance, comprising a 5- or 6-membered heteratom-containing ring, or an aryl group, and may include fused rings. The heteroaryl may have 1 or 2 heteroatoms which may be the same or different and are, eg, selected from N, S and O. Suitable heteroaryl groups are for instance furyl groups, for instance 2- or 3-furyl, thiazyl, pyridyl or, preferably, thienyl groups. Where $R^1$ is thienyl, it may be a 3-thienyl group or a 2-thienyl group. 2-Thienyl groups are often found to be more reactive in the new process. Any of the heteroaryl groups may have substituents in the ring(s), particularly substituents which enhance the electron rich nature of the ring. Such substituents include lower alkyl, usually methyl, and lower alkoxy groups. Halogen substituents may also be present in the ring.

An aryl group represented by $R^1$ is generally a phenyl group having one or more electron rich substituents, such as alkoxy groups, alkyl groups, halo atoms or aryl groups. An unsubstituted phenyl group or phenyl substituted by substituents which are not electron rich may be useful as $R^1$ in combination with other electron rich substituents as groups $R^3$-$R^6$.

Although $R^3$ and $R^4$ or $R^5$ and $R^6$ may sometimes both be hydrogen, preferably at least one, and preferably both of them are not hydrogen i.e. represent alkyl groups. Such alkyl groups are generally lower alkyl, for instance $C_{1-6}$ alkyl, most preferably methyl or ethyl. Alkyl groups include cycloalkyl groups. Alkenyl groups represented by $R^3$-$R^6$ are generally lower alkenyl groups, for instance $C^2$-$C^6$ alkenyl Suitable groups are for instance vinyl and allyl groups. Aryl groups represented by $R^3$-$R^6$ are, for instance, optionally substituted phenyl groups.

In the compound of the formula I where one of $R^3$-$R^6$ represents hydrogen, it is preferable that the remaining groups represent groups other than hydrogen. It is particularly preferred for none of the groups $R^3$-$R^6$ to represent hydrogen.

The process is carried out in a solvent which is inert in the reaction, including towards the silica. For instance it has been found that the use of ether as the solvent may lead to no reaction since the ether adsorbs onto the silica thereby deactivating it. A suitable solvent is carbon tetrachloride although other solvents such as dichloromethane and tetrachloroethylene would be expected also to be useful.

The process of the invention may be used to selectively ring open one cyclopropane compound in a mixture of compounds, for instance which is the product mixture from a previous reaction. For instance it has been found that a product mixture of syn and anti-isomers (with respect to the $R^1$ group) produced by the trapping of halocarbenes by ethylenically unsaturated compounds, such as are described in our application filed even date herewith (reference number T 1152), can be contacted with silica to ring open one of the isomers, the syn-isomer, and leave the anti-isomer intact. It is found that the silica may simultaneously adsorb unwanted components of the reaction mixture and so provide a purified product mixture.

The process may be carried out by contacting the particulate silica with the solution of cyclopropane in a stirred vessel, for a period of a few minutes to several hours, at a raised or, preferably at ambient temperature.

In such a process the silica is generally removed from the product mixture by filtration and the compound produced recovered from solution. Alternatively, the reaction may be carried out by passing the solution of the cyclopropane through a column containing silica.

It is believed that the ring opening reaction through a column containing silica proceeds with simultaneous departure of leaving group $(R^2)^-$ to produce an allylic cation. Depending on the reaction conditions and the components present in the reaction mixture, and on the substituents on the cation, it may either be intercepted by an anion present in the system, for instance the $(R^2)^-$ which is produced in the first step or another nucleophilic species present, to form an allyl compound, or a hydrogen ion may be lost to provide the diene. Also an allyl product may subsequently be converted by, eg, dehydrohalogenation, to provide the diene. An allyl product may consist of a number of isomers, depending on which of the carbon atoms of the allylic cation intermediate is attacked by the nucleophilic compound.

The process of the invention is far more convenient than other ring opening processes to carry out and may give the product in a good yield and in a form which is easily recoverable.

The products of the reaction may be useful in themselves or may be useful as intermediates to produce other compounds having various applications. For instance the beta-thienyl-allylic amines described in EP-A-187390 which are useful as inhibitors of dopamine beta-hydroxylase and thus as antihypertensive agents, may be produced from the corresponding halide by the Gabriel synthesis as disclosed in that reference.

The dienes may for instance be reacted in a Diels-Alder reaction to provide various $C_6$-membered ring derivatives. The products of such a reaction would be useful in a wide range of applications.

It is believed that the products formed from thienyl cyclopropane derivatives are novel.

Accordingly the present invention includes compounds of the formula II:

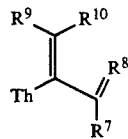

wherein Th is thienyl, $R^8$ is an alkylidene or aralkylidene group, and $R^7$, $R^9$ and $R^{10}$ are independently selected from hydrogen, alkyl, aralkyl, aryl, heteroaryl and alkenyl groups, provided that when $R^8$ is benzylidene, $R^7$ is phenyl, and $R^9$ and $R^{10}$ are both hydrogen Th is not methyl substituted thienyl. Preferably $R^7$ is not aryl when $R^8$ is aralkylidene, more preferably is $R^7$ hydrogen, alkyl or alkenyl.

Preferably $R^9$ and $R^{10}$ are each other than hydrogen and more preferably $R^7$ is also other than hydrogen.

Th is preferably a 2- or 3-thienyl group, which may optionally be substituted in the thiophene ring. Thus it may have one or more substituents selected from halogen atoms, lower alkyl groups, lower alkoxy groups, halo atoms and aryl groups.

$R^8$ is usually a methylene group. Preferably each of $R^7$, $R^9$ and $R^{10}$ are lower alkyl groups that can alternatively be aryl, aralkyl or alkenyl groups. Any of the alkyl, aralkyl, aryl or alkenyl groups may be substituted, for instance by lower alkoxy, halogen or aryl groups.

Accordingly the present invention also includes compounds of the formula III:

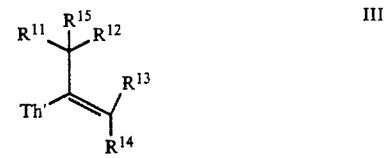

wherein Th' is thienyl, and $R^{15}$ is a halogen atom and $R^{11}$ to $R^{14}$ are each independently selected from hydrogen, alkyl, aralkyl, aryl, heteroaryl and alkenyl groups, provided at least one is other than hydrogen.

Th' can have any of the definitions given above for Th. At least one, and often all, of $R^{11}$ to $R^{14}$ is other than hydrogen, usually lower alkyl. $R^{15}$ is preferably bromine or, most preferably, chlorine.

The novel compounds may be produced by the novel process described above.

The following examples illustrate the invention:

EXPERIMENTAL DETAILS

Petroleum refers to the fraction boiling at 40°-60° C. Reagents obtained commercially were used without further purification unless otherwise stated. n-Butyl lithium was obtained from Aldrich Chemical Company as a ca. 1.5 M solution in hexane. The accurate molarity was determined by titration with diphenylacetic acid. All manipulations involving alkyl lithiums were conducted under a nitrogen atmosphere. Organic solutions were dried using anydrous magnesium sulphate and solvents generally removed on a rotary evaporator at ca. 14 mmHg. T.l.c. was performed on Schleicher and Shuell F 1500 LS 254 silica-gel plates.

Medium pressure chromatography was conducted using Merck 7736 silica gel and gravity chromatography using gravity silica or Brockmann activity II alumina.

Melting points were determined using a Kofler hot stage apparatus and are uncorrected. Elemental analysis was determined with a Carlo - Erba Instrumentazione model 1106 elemental analyser. Infra red spectra were recorded as thin film (liquids) or a potassium bromide disc (solids), on a Nicolet 20 SX B Fourier transform spetrometer and the type of absorption (strong, medium or weak) is quoted in the text. $^1$H N.m.r. spectra were recorded at 60 MHz using a Hitachi Perkin Elmer R-24B spectrometer, at 200 MHz on a Bruker WP 200, or at 300 MHz using a Bruker WP 300-WB instrument. The order of citation in parenthesis in the text is: number of nuclei (by integration), muliplicity and coupling constant. The abbreviation $W_{\frac{1}{2}}$ refers to the width at half height of a broad signal and unless otherwise stated, spectra were recorded at 60 MHz. Mass spectra, elec-

EXAMPLE 1 a) 3-Methyl-2-dichloromethylthiophene

3-Methyl-2-thiophenecarboxaldehyde (3.05 g, 24 mmol) in dry ether (10 ml) was added dropwise to a stirred suspension of phosphorus pentachloride (5.0 g, 24 mmol) in dry ether (30 ml) at 0° C. After 10 min at 0° C., the mixture was filtered and the solvent removed to leave a black oil which was taken up in light petroleum (30 ml). After standing for 1 h, the clear liquid was decanted from a black residue and filtered. The process was repeated several times until a clear, pale yellow solution resulted. Removal of the solvent afforded crude 3-methyl-2-dichloromethylthiophene (4.4 g) in almost quantitative yield, as a black oil containing ca. 5% aldehyde (Found M+: 179.9574. $C_6H_6SCl_2$ require M, 179.9566) which showed $\delta_H$ (CCl$_4$) 2.26 (3H, s), 6.67 (1H, d, J 5 Hz), 6.84 (1H, s), 7.12 (1H, d, J 5 Hz); m/z 180 (M+), 145 (M+-Cl).

The product polymerises rapidly at room temperature and is extremely susceptible to hydrolysis; it was therefore used immediately without purification.

b) 1-Chloro-1-(3-methylthien-2-yl)-2,2-dimethylcyclopropane. (Compound I, $R^1$=3-methylthien-2-yl, $R^2$=Cl, $R^3$=$R^4$=H, $R^5$=$R^6$=Me)

Potassium-t-butoxide (5.0 g, 44 mmol) was added over 10 min to a stirred solution of crude 3-methyl-2-dichloromethylthiophene produced as in a) (4.0 g, 22 mmol) and excess 2-methylpropene (about 10 ml, 7 g, 0.13 mol) in dry ether (40 ml) at 0° C. After 30 min at 0° C. the mixture was diluted with water (10 ml), the ether extract was separated and the ether removed. The residue was taken up in light petroleum (30 ml) and washed with water (3×30 ml). The organic extract was dried and the solvent evaporated to yield the crude cyclopropane as a red/brown oil (2.3 g, 26%) which was free from aldehyde and dichloride. A portion of this product (1.25 g) was distilled at reduced pressure (oven temperature 65° C. at 0.1 mmHg) to afford 1-chloro-1-(3-methylthien-2-yl)-2,2-dimethylcyclopropane (0.75 g, 16%) as a colourless oil which was pure by n.m.r. (Found M+: 200.0421. $C_{10}H_{13}SCl$ requires M, 200.0426) which showed $\delta_H$ (CCl$_4$) 0.92 (3H, s), 1.20 (2H, narrow m), 1.45 (3H, s), 2.20 (3H, s), 6.65 (1H, d, J 5 Hz), 6.90 (1H, d, J 5 Hz); m/z 200 (M+), 185 (M+-CH$_3$), 165 (M+-Cl).

c) Silica gel promoted ring opening of 1-chloro-1-(3-methyl-thien-2-yl)-2,2-dimethylcyclopropane The cyclopropane produced in b) (0.40 g, 2.0 mmol) was stirred with gravity silica (0.15 g) in carbon tetrachloride (10 cm$^3$) at 20° C. The silica developed a purple/black coloration within 30 min while the solution remained colourless. After 18 h at 20° C. no starting material remained. The silica was removed by filtration and the carbon tetrachloride evaporated to give a product characterised as 1-chloro-2-(3-methylthien-2-yl)-3-methylbut-2-ene (0.33 g, 82%) as the only product, which was pure by n.m.r. (Found: M+ +200.0417. $C_{10}H_{13}SCl$ requires M, 200.0426) which showed $\nu_{max}$ (film) 708 s, 1256 m, 1444 m, 1700 m and 29922 m cm$^{-1}$; $\delta_H$ (CCl$_4$) 1.65 (3H, s), 1.98 (3H, s), 2.06 (3H, s), 4.20 (2H, s), 6.72 (1H, d, J 5 Hz), 7.03 (1H, d, J 5 Hz); m/z 200 (M+), 165 (M+-Cl).

EXAMPLE 2 a) 3-Phenyl-2-thiophenecarboxaldehyde

3-Phenyl-2-thiophenecarboxaldehyde was prepared by Vilsmeier formylation of 3-phenylthiophene as described by S. Gronowitz and N. Gjos in Acta. Chem. Scand. 1970 24 99 and 1972 26 1851. Although this reaction is reported to give a 94:6 ratio of 2,3 to 2,4 substituted compounds, the product, after chromatography, appeared to be only one isomer and was idential to an authentic sample of 3-phenyl-2-thiophenecarboxaldehyde.

b) 3-Phenyl-2-dichloromethylthiophene

3-Phenyl-2-thiophenecarboxaldehyde produced as in a) (2.24 g, 12 mmol) in ether (20 ml) was added dropwise to a stirred suspension of phosphorus pentachloride (2.6 g, 12.5 mmol) in dry ether (25ml) at 0° C. The mixture was stirred at 0° C. until the solution became clear (30 min) and then poured onto ice-water (200 ml). After separating the layers, the ether was evaporated and replaced with light petroleum (30 ml). The organic extract was washed with saturated sodium hydrogen carbonate solution (2×50 ml) followed by water, dried, and the solvent evaporated to yield 3-phenyl-2-dichloromethylthiophene (2.40 g, 83%) as an orange syrup. The product was pure by t.l.c. and n.m.r. (Found M+: 241.9711. $C_{11}H_8SCl_2$ requires M, 241.9724) and showed $\nu_{max}$ (film) 700s, 736s, 772s, 1178m and 1489m cm$^{-1}$; $\delta_H$ (CCl$_4$) 6.70 (1H, s), 6.75 (1H, d, J 5 Hz), 7.2 (6H narrow m); m/z 242 (M+) 207 (M+-Cl).

c) 1-Chloro-1-(3-phenylthien-2-yl)-2,2-dimethylcyclopropane (Compound I, $R^1$=3-phenylthien-2-yl, $R^2$=Cl, $R^3$=$R^4$=H, $R^5$=$R^6$=Me)

Potassium-t-butoxide (0.25 g, 2.2 mmol) was added in one portion to a stirred solution containing 3-phenyl-2-dichloromethylthiophene produced in b) (0.25 g, 1.0 mmol) and 2-methylpropene (1.0 g, 18 mmol) in dry ether (10 ml) at 0° C. After 5 min the solution was allowed to attain room temperature and stirred for an additional 30 min. Light petroleum (20 ml) was added, followed by water (50 ml) and the organic phase was separated and washed several times with water. Work up as in example 11b) above and stirring with silica (0.5 g) in CCl$_4$ (10 ml) for 10 min at room temperature followed by filtration and evaporation removed trace impurities to afford 1-chloro-1-(3-phenylthien-2-yl)-2,2-dimethyl-cyclopropane as a clear syrup (2.00 g, 75%) (Found M+: 262.0594. $C_{15}H_{15}SCl$ requires M, 262.0583) which showed $\nu_{max}$ (film) 698s, 728s, 1067m, 1449m, 1490m, 2926m and 2954m cm$^{-1}$; $\delta_H$ (CCl$_4$) 0.68 (3H, s), 0.99 (1H, d, J 6 Hz), 1.15 (1H, d, J 6 Hz), 1.35 (3H, s), 6.85 (1H, d, J 6 Hz), 7.0–7.6 (6H, m); m/z 262 (M+), 247 (M+-CH$_3$), 227 (M+-Cl).

d) Silica gel promoted ring opening of 1-chloro-1-(3-phenyl-thien-2-yl)-2,2-dimethylcyclopropane The cyclopropane produced in c) (0.15 g, 0.57 mmol) was stirred with silica (50 mg) in carbon tetrachloride (5 cm$^3$) at 20° C. The reaction was followed by n.m.r. After 30 h no starting material remained. The mixture was filtered to remove the black silica and the solvent removed at reduced pressure to afford 1-chloro-2-(3- phenylthien-2-yl)-3-methylbut-2-ene (0.13 g, 85%) as a clear dark oil which was pure by n.m.r which showed $\nu_{max}$ (film) 698s, 769m, 1261m, 1446m, 1488m, 1601m, 2907w, 2985w and 3030w cm$^{-1}$; $\delta_H$(CCl$_4$) 1.51 (3H, s), 1.88 (3H, s), 4.11 (2H, s), 7.2 (7H, m).

EXAMPLE 3 a)

1-Bromo-1-(2,5-dibromothien-3-yl)-2,2,3,3-tetramethylcyclopropane. (Compound I, R$^1$=2, 5-dibromothien-3-yl, R$^2$=Br,R$^3$=R$^4$=R$^5$=R6=Me)

Potassium-t-butoxide (2.2 g, 20 mmol) was added over 5 min to a rapidly stirred solution of 2,5-dibromo-3-dibromomethylthiophene (produced by bromination of 3-methylthiene) (2.0 g, 4.8 mmol) and 2,3-dimethylbut-2-ene (3.2 g 38 mmol) in dry ether (20 cm$^3$) at 0° C. The reaction was shown by n.m.r. to be 70% complete after 10 min at 0° C. After vigorous stirring for a further 20 min at 20° C., the gelatinous mixture was poured onto water (100 ml) and extracted with light petroleum (20 ml). The organic extract was washed with water (3×30 ml), dried, and the solvent removed. The product was a viscous oil which solidified on standing for 24 h. Recrystallisation from petroleum at ca. −20° C. afforded the title compound as a pale yellow powder (1.69 g, 84%), m.p. 78°–80° C. (Found M$^+$: 413.8317; C, 31.7; H, 2.7. C$_{11}$H$_{13}$Br$_3$S requires M, 413.8289; C, 31.7; H, 3.1%) which showed $\nu_{max}$(KBr) 731m, 825s, 1376m, 1447w, 2869w, 2917w and 2943w cm$^{-1}$; $\delta_H$ (200 MHz; CDCl$_3$) 1.11 (3H, s), 1.13 (3H, s), 1.34 (3H, s), 1.40 (3H, s) and 6.87 (1H, s); m/z 414 (M$^+$), 335 (M$^+$-Br), 256 (M$^+$-2Br), 177 (M -3Br).

b) Silica gel promoted ring opening of 1-bromo-1(2,5-dibromo-thien-3-yl)-2,2,3,3-tetramethylcyclopropane 1-Bromo-1-(2,5-dibromothien-3-yl)-2,2,3,3-tetramethyl cyclopropane produced in a) (0.10 g, 0.24 mmol) was stirred with gravity silica 1.0 g) in carbon tetrachloride (3ml) for 18 h at 20° C. During this time the silica developed a purple/black coloration while the solution remained colourless. The mixture was filtered and the solvent removed to afford pure 2,4-dimethyl-3-(2,5-dibromothien-3-yl)penta-1,3-diene (compound II, Th=2,5-dibromothien-3-yl, R$^7$=R$^9$R$^{10}$=Me, R$^8$=CH$_2$) (64 mg, 79%) as a clear yellow syrup (Found: MH$^+$ 334.8973. C$_{11}$H$_{12}$SBr$_2$ requires MH, 334.9096) which showed $\nu_{max}$ (film) 899s, 986s, 1136s, 1179s, 1442m, 1528m, 2910m, 2930 and 2968w cm$^{-1}$; $\delta_H$(3H, s), 1.17 (3H, s), 1.83 (3H, s), 4.79 (1H, br s, W$_{\frac{1}{2}}$ 6 Hz), 4.95 (1H, br s, W$_{\frac{1}{2}}$ 6 Hz), 6.60 (1H, s); m/z 335 (MH$^+$), 257 (M$^+$-Br), 176 (M$^+$-2Br).

EXAMPLE 4 a)

1-Bromo-1-(2,5-dibromothien-3-yl)-2,2-dimethyl-cyclopropane (Compound I, R$^1$=2,5-dibromothien-3-yl, R$^2$=Br, R$^3$=R$^4$=H, R$^5$=R$^6$=Me)

Replacement of 2,3-dimethylbut-2-ene by 2-methylpropene in the process of Example 3a) gave a red oil (1.61 g, 85%) which was pure by n.m.r. Chromatography on neutral silica with petroleum as eluent afforded the title compound as a pale yellow oil (1.3, 66%) (Found M$^+$: 385.8007. C$_9$H$_9$Br$_3$S required M, 385.7976) which showed $\nu_{max}$ (film) 659s, 992s, 1062m, 1115m, 1442m, 2924s and 2954s cm$^{-1}$; $\delta_H$ (CCl$_4$) 1.02 (3H, s), 1.2 (2H, br m, W$_{\frac{1}{2}}$ 12 Hz), 1.50 (3H, s), 6.77 (1H, s); m/z 386 (M$^+$), 307 (M$^+$-Br), 228 (M$^+$-2Br), 149 (M$^+$-3Br).

b) Silica gel promoted ring opening of 1-bromo-1-(2,5-dibromothien-3-yl)-2,2-dimethylcyclopropane The cyclopropane produced in Example 4a) (0.50 g, 1.3 mmol) was stirred with silica (1.0 g) in carbon tetrachloride (10 cm$^3$) at 60°–80° C. The silica became black while the solution remained colourless. After 10 h, $^1$H m.m.r. showed that no cyclopropane remained. The solution contained what was believed to be 1-bromo-2-(2,5-dibromothien-3-yl)-3-methylbut-2-ene, 1-bromo-2-methyl-3-(2,5-dibromo-thien-3-yl)-trans-but-2-ene and 1-bromo-2-methyl-3-(2,5-dibromo-thien-3-yl) cis-but-2-ene in a 1:1:1 ratio. The solution was filtered and fresh silica (3.0 g) was added. Heating at 60°–80° C. for a further 10 h did not give any other products. Stirring at 20° C. with frequent changes of silica (every 2 days) resulted in slow conversion of the three allylic bromides to a diene. After 10 days the solution was filtered and the solvent removed to give 2-(2,5-dibromo-thien-3-yl)-3-methylbuta-1,3-diene (compound II, Th=2,5-dibromothien-3-yl, R$^9$=R$^{10}$=H, R$^7$Me R$^8$=CH$_2$ (0.14 g, 34%) as a clear oil (Found: M$^+$305 8706. C$_9$H$_8$SBr$_2$ requires M, 305.8715) which showed $\nu_{max}$ (film) 786s, 902s, 1000s, 1185w, 1422w, 1533w, 1594w, 2923w cm$^{-1}$; $\delta_H$ (CCl$_4$) 94 (3H, s), 4.74 (1H, s), 5.00 (1H, s), 5.08 (1H, s), 5.40 (1H, s) 6.64 (1H, s); m/z 306 (M$^+$), 227 (M$^+$-Br), 148 (M$^+$-2Br).

EXAMPLE 5 a) 2,5-Diethyl-3-thiophenecarboxaldehyde

Titanium tetrachloride (8.0 cm$^3$, 70 mmol) was added slowly under nitrogen to a stirred solution of 2,5-diethylthiophene (6.0 g, 43 mmol) in dichloromethane (25 ml) at 0° C. After 10 min, 1,1-dichloromethyl methyl ether (5.0 g, 43 mmol) was added dropwise causing a vigorous reaction and the evolution of hydrogen chloride The dark mixture was stirred at 0° C. for 30 min followed by 1 h at 20° C. and then poured onto ice water (100 ml). The organic phase was separated, the aqueous solution was extracted with dichloromethane (3×20ml) and the combined organic extracts were washed with 10% aqueous sodium hydroxide (2×50 ml) and dried. Removal of the solvent gave a brown oil which was distilled at reduced pressure to yield 2,5-diethyl-3-thiophenecarboxaldehyde (4.1 g, 57%) as a colourless oil which darkened rapidly, b.p. 72° C. at 0.3 mmHg (Found M$^+$:168.0620. C$_9$H$_{12}$SO requires M, 168.0609) which showed $\nu_{max}$ (film) 1195m, 1387m, 1457m, 1676s, 2875m, 2933m and 2970s cm$^{-1}$; $\delta_H$ (CCl$_4$) 1.28 (3H, t, J 8 Hz) 1.32 (3H, t, J 8 Hz), 2.75 (2H, q, J 8 Hz), 3.13 (2H, q, J 8 Hz), 6.93 (1H, s), 9.85 (1H, s); m/z 168 (M$^+$) 153 (M$^+$-CH$_3$), 139 (M$^+$-C$_2$H$_5$).

b) 2,5-Diethyl-3-dichloromethylthiophene 2,5-Diethyl-3-thiophenecarboxaldehyde produced in a) (2.6 g, 15 mmol) in ether (30 ml) was treated with phosphorus pentachloride (3.4 g, 16 mmol) in ether (30 ml) at 20° C. After 30 min, the solution was poured onto ice-water (5 ml) and petroleum (20 ml) was added. Work up as in example 8b) afforded 2,5-diethyl-3-dichloromethylthiophene (2.9 g, 84%) as a clear oil which was pure by n.m.r. (Found M$^+$: 222.0015 C$_9$H$_{12}$SCl$_2$ requires M, 222.0037) which showed $\nu_{max}$ (film) 734s, 1202m, 1457m, 1675m, 2932m and 2970s cm$^{-1}$; $\delta_H$(CCl$_4$) 1.28 (6H, t, J 7 Hz), 2.71 (4H, br q. J 7 Hz), 6.51 (1H, s), 6.77 (1H, br s, W$_\frac{1}{2}$ 4 Hz); m/z 222 (M$^+$), 187 (M$^+$-Cl).

c)

1-Chloro-1-(2,5-diethyl-thien-3-yl)-2,2,3,3-tetramethylcyclopropane Compound I, R$^1$=2,5-diethylthien-3-yl, R$^2$=Cl, R$^3$=R$^4$=R$^5$=R$^6$=Me)

In a process similar to that described in example 7, potassium-t-butoxide (0.25 g, 2.2 mmol) was added in one portion to a rapidly stirred solution of 2,5-diethyl-3-dichloromethylthiophene produced in b) (0.23 g, 10.0 mmol) and 2,3-dimethylbut-2-ene (1.0 g, 12 mmol) at 20° C. After 1 h at ambient temperature, water (30 ml) and light petroleum (30 ml) were added. The organic extract was washed with more water, dried, and evaporated to give the crude cyclopropane as a dark oil. Rapid chromatography on silica (eluent: light petroleum -ethyl acetate (5:1)) yielded only one product, identified as 2,4-dimethyl-3-(2,5-diethylthien-3-yl)-penta-1,3- diene (compound II, Th=2,5-diethylthien-3-yl, R$^8$=CH$_2$, R$^7$=R$^9$=R$^{10}$=Me) (30 mg, 13%) (Found M+234.1448. C$_{15}$H$_{22}$S requires M, 234.1442) which showed $\nu_{max}$ (film) 837w, 894m, 1456m, 1631w, 2929m and 2967s cm$^{-1}$; $\delta_H$ (CCl$_4$) 1.2 (6H, m), 1.48 (3H, s), 1.57 (3H, s), 1.77 (3H, s), 2.59 (4H, m), 4.64 (1H, br s, W$_\frac{1}{2}$ 6 Hz), 4.81 (1H, br s, W$_\frac{1}{2}$ 6 Hz), 6.12 (1H, s); m/z 234 (M$^+$), 219 (M$^+$-CH$_3$), 205 (M$^+$-C$_2$H$_5$).

EXAMPLE 6 a) 3-Ethyl-2-thiophenecarboxaldehyde

Lithium aluminium hydride (0.3 g, 9.0 mmol) was added in small portions over 10 min to a stirred solution of 3-ethyl-2-cynothiophene (formed by the electrophilic cyanation of 3-ethylthiophene with chlorosulphonyl isocyanate and dimethyl formamide as described by Gronowitz et al in Acta Chem. Scand. B31 (1977) 771-780) (1.00 g, 7.3 mmol) in ether (30 ml). After 2 h at 20° C. followed by 1 h at 30° C., the mixture was quenched with water (2 ml). Light petroleum (30 ml) was added and the organic extract washed with 10% hydrochloric acid (50 ml) followed by water (30 ml). After drying, the solvent was removed to give an oil which contained several products. This procedure was repeated on a larger scale using 2.22 g (16.2 mmol) of the starting compound. The product mixtures were combined and purified by chromatography on silica, eluting with light petroleum-ethyl acetate (4:1) to provide 3-ethyl-2-thiophenecarboxaldehyde (0.36 g, 11%) as a clear yellow oil (Found M : 140.0297. C$_7$H$_8$SO requires M, 140.0296) which showed $\nu_{max}$ (film) 668m, 1199m, 1243m, 1425m, 1657s, 2873m and 2971m cm$^{-1}$; $\delta H_H$(CCl$_4$) 1.27 (3H, t, J 8 Hz), 2.96 (2H, q, J 8 Hz), 6.82 (1H, d, J 5 Hz), 7.40 (1H, d, J 5 Hz), 9.77 (1H, s); m/z 140 (M ), 125 (M$^+$-CH$_3$), 111 (M$^+$-CHO).

b) 3-Ethyl-2-dichloromethylthiophene

3-Ethyl-2-thiophenecarboxaldehyde produced in a) (0.30 g, 2.1 mmol) in ether (15 ml) was added dropwise to a stirred suspension of phosphorus pentachloride (0.53 g, 2.5 mmol) in ether (15 ml) at 20° C. After 15 min at 20° C. no aldehyde remained (n.m.r.). The ether was evaporated and replaced with light petroleum (40 ml). The solution was poured onto ice water (50 ml), the organic phase was separated and quickly washed with ice-cold saturated sodium hydrogen carbonate (20 ml) followed by water. After drying, the solvent was removed and replaced by petroleum. After standing overnight at −10° C., the solution was decanted from the black residue and evaporated to afford 3-ethyl-2-dichloromethylthiophene (0.33 g, 80%) as a clear yellow oil which contained a minor amount (ca. 10%) of the aldehyde (Found M$^+$: 193.9748. C$_7$H$_8$SCl$_2$ requires M, 193.9724) which showed $\delta_H$ (CCl$_4$) 1.23 (3H, t, J 7 Hz), 2.66 (2H, q, J 7 Hz. 6.72 (1H, d, J 5 Hz) 6.85 (1H, s), 7.18 (1H, d, J 5 Hz); m/z 194 (M$^+$), 159 (M$^+$-Cl).

This material was susceptible to hydrolysis and thermal decomposition and so was used immediately.

c)

1-Chloro-1-(3-ethylthien-2-yl)-2,2,3,3-tetramethylcyclopropane

Potassium-t-butoxide (0.30 g, 2.7 mmol) was added in small portions over 5 min to a stirred solution of crude 3-ethyl-2-dichloromethylthiophene produced in b) (0.14 g, 0.72 mmol) and 2,3-dimethylbut-2-ene (1.0g, 12 mmol) in ether (10 ml) at 20° C. After 15 min the solution was poured onto water (50 ml), light petroleum (40 ml) was added and the organic extract was washed several times with water. The product was dried and the solvent removed to yield a clear red/brown oil provisionally identified as 1-chloro-1-(3-ethylthien-2-yl)-2,2,3,3-tetramethylcyclopropane (compound I, R$^1$=2-ethylthien-2-yl, R$^2$Cl, R$^3$=R$^4$=R$^5$=R$^6$=Me) (ca. 90 mg, 50%) which showed $\delta_H$(CCl$_4$) 1.0-1.5 (15H, complex m), 2.55 (2H, q, J 7 Hz), 6.75 (1H, d, J 5 Hz), 7.0 (1H, d, J 5 Hz). Rapid chromatography through a small bed of silica, eluting with hexane, resulted in ring opening and some decomposition. Only one product was eluted and characterised as 2,4-dimethyl-3-(3-ethylthien-2-yl)-penta-1,3-diene (compound II, Th=3-ethylthien-2-yl, R$^7$=R$^9$=R$^{10}$=Me R$^8$=CH$_2$) (30 mg, 20%) (Found M$^+$: 206.1146. C$_{13}$H$_{18}$S requires M, 206.1129) which showed $\nu_{max}$ (film) 899s, 1370m, 1443s, 1632w, 2854s, 2931s, 2966s and 3077w cm$^{-1}$; $\delta_H$ (CCl$_4$) 1.13 (3H, t, J 7 Hz), 1.60 (3H, s), 1.68 (3H, s), 1.88 (3H, s), 2.40 (2H, q, J 7 Hz), 4.77 (1H, br s, W$_\frac{1}{2}$ 6 Hz), 4.90 (1H, br s, W$_\frac{1}{2}$ 6 Hz), 6.72 (1H, d, J 5 Hz), 6.99 (1H, d, J 5 Hz); m/z 206 (M$^+$), 191 (M$^+$-CH$_3$).

EXAMPLE 7 a) 3-Dichloromethylthiophene

3- Thiophenecarboxaldehyde (10.0 g, 89 mmol) in ether (30 ml) was added dropwise to a stirred suspension of phosphorus pentachloride (20 g, 96 mmol) in ether (100 ml). After 15 min at 0° C. the clear solution was poured onto ice-water, washed with saturated sodium hydrogen carbonate solution (2×100 ml) followed by water (100 ml), and dried. Removal of the solvent yielded pure 3-dichloromethylthiophene (12.2 g, 82%) as a clear pale yellow oil (Found M+ 165.9406 C$_5$H$_4$SCl$_2$ requires M, 165.9410) which showed $\nu_{max}$ (film) 715s, 771m, 834m, 1153m, 1421m, 1690w and 3110m cm$^{-1}$; $\delta_H$ (CCl$_4$) 6.67 (1H, s), 7.18 (2H, narrow m), 7.30 (1H, narrow m); m/z 166 (M$^+$), 433 (M$^+$-Cl).

The product could be stored either neat or in solution at room temperature without decomposition.

b) 1-Chloro-1-(thien-3-yl)-2,2,3-trimethylcyclopropane

Potassium-t-butoxide (2.0 g, 18 mmol) was added over 5 min to a rapidly stirred solution of 3-dichloromethylthiophene produced as in a) (1.00 g 6.0 mmol) in dry ether (10–20 ml) at 0° C., containing 2-methylbut-2-ene (>8 equiv.). After 1 h at 20° C., the products were worked up as in Example 3a) to give oils which contained no starting material, although traces of t-butanol were present. The product was a mixture of geometrical isomers (anti/syn = 1.31) (0.7 g, 59%). Kugelrohr distillation (oven temperature 80° C. at 0.1mmHg) afforded the product as a colourless oil (0.47 g, 40%) with no change in the isomer ratio (Found M+ 200.0431. $C_{10}H_{13}SCl$ requires M, 200.0426). Chromatography on silica with petroleum as eluent resulted in decomposition of the minor (syn) isomer affording pure major anti-isomer (27%) (Found M+ 200.0437. $C_{10}H_{13}SCl$ requires M, 200.0426) which showed $v_{max}$ (film) 752s, 773s, 838s, 1453m, 2927s, 2950s and 2996m cm$^{-1}$; $\delta_H$ (200 MHz; CDCl$_3$) 0.85 (3H, s), 1.22·(3H, s), 1.24 (4H, m), 7.11 (2H, m), 7.24 (1H, q, J 3, 5 Hz); m/z 200 (M+), 185 (M -CH$_3$), 165 (M+-Cl). From the $^1$H n.m.r. of the mixture, the minor (syn) isomer showed $\delta_H$ (200 Mz; CDCl$_3$) 0.94 (3H, s), 1.05 (3H, d, J 6.5 Hz), 1.35 (1H, q, J 6.5 Hz), 1.48 (3H, s), 7.05 (1H, dd, J 1.5, 5.0 Hz) and 7.25 (2H,m); m/z 200 (M+), 185 (M+-CH$_3$), 165 (M+-Cl).

EXAMPLE 8

The previous example was repeated replacing the 2-methylbut-2-ene by 2-methylpropene to provide the corresponding 2,2-dimethyl cyclcopropane derivative. The product was stirred with gravity silica in carbon tetrachloride in a manner similar to that described in Example 1c). After 5 days at 20° C. the compound 1-chloro-2-(thien-3-yl)-3-methylbut-2-ene in a yield of 47%.

EXAMPLE 9

Replacement of the 2-methylbut-2-ene in Example 7 by 2.3-dimethylbut-2-ene gave the 2,2,3,3,-tetramethyl cyclopropane derivative. This was reacted in carbon tetrachloride solution in the presence of silica at 20° C. for 3 days in a manner similar to that described in Example 1c). The product was identified as 3-(thien-3-yl)-2,4-dimethylbut-1,3-diene (compound II, Th=thien-3-yl, $R^7=R^9=R^{10}=Me$ $R^8=CH_2$). The yield was 83%.

EXAMPLE 10 a) 3-Chloro-3-(thien-2-yl)-3H-1,2-diazirine

2-Amidinothiophene hydrochloride (produced in the manner disclosed in Acta Chem. Scand. B31 771 (1977) by Gronowitz et al) (3.00 g, 18.5 mmol) and lithium chloride (5 g) were dissolved in dimethyl sulphoxide (50 ml) with stirring. When the solution became clear, petroleum (50 ml) was added. Aqueous sodium hypochlorite (10 mol equiv.) containing dissolved sodium chloride (20 g) was then added rapidly so the temperature of the reaction mixture increased to 35° C. for 8 min then 30° C. for 10 min. The petroleum extract was separated and the aqueous solution extracted with petroleum (3 × 40 ml). The combined petroleum extracts were washed with water (200 ml), dried, and the solvent removed to yield 3-chloro-3-(thien-2-yl) diazirine in 65% yield as a clear orange oil which was pure by $^1$H n.m.r. and t.l.c., the N-chlcro amidine not being extracted under these conditions. The diazirine exhibited a characteristic N=N stretching band in the i.r. spectrum at 1566 cm$^{-1}$ while the $^1$H n.m.r. contained three multiplets at $\delta$ 6.75, $\delta$ 6.95 and $\delta$ 7.28. The neat product darkened within minutes at room temperature, decomposing exothermically with the evolution of nitrogen. After ca, 30 min. a black oil solid remained; chromatography afforded bright yellow needles of the azine 1,4-dichloro-1,4-di(thien-2-yl) 2,3-diazabuta-1,3-diene, the $^1$H n.m.r. spectrum of which showed a double doublet at 7.10, a doublet at $\delta$ 7.48 and a doublet at $\delta$ 7.72, each integrating for two protons. The diazirine could be stored for several days at −10° C. when neat, or longer if diluted with a non polar solvent.

b) 7-Chloro-7-(thien-2-yl)norcarane

The diazirine a) (0.60 g), 3.8 mmol) in cyclohexene (20 cm$^3$, 0.2 mol) was heated at 40°–60° C. for 2 h. After evaporating the solvent, the crude product, a mixture of isomers, was rapidly chromatographed on silica with light petroleum as eluant. Decomposition occured during chromatography, however a single isomer was eluted and identified as pure anti-7-chloro-7-(thien-2-yl)-norcarane (0.22 g, 27%), a colourless oil. It was assumed that the syn-isomer was decomposed.

EXAMPLE 11

Replacement of the cyclohexene by 2,3-dimethylbut-2-ene in part b of the previous example provided a product mixture which included 1-chloro-1-(thien-2-yl)-2,2,3,3-tetramethyl cyclopropane. A solution of this compound in carbon tetrachloride was contacted with silica and stirred at 20° C. for 5 h, in a manner similar to that in Example 1b). The product mixture contained 3-(thien-2-yl)-2, 4-dimethylbut-1,3-diene. This was subsequently reacted with tetracyanoethylene in a Diels-Alder reaction to produce the corresponding 6-membered ring product.

EXAMPLE 12

I Preparation of diohloromethylphenyl compounds a) 4-Methoxy(dichloromethyl)benzene

4-Methoxybenzaldehyde (5.0 g) in ether (50 ml) was added dropwise to phosphorus pentachloride (3.6 mol. equiv.) stirred in dry ether (50 ml) at 0° C.; after 30 m, the cooling bath was removed, and the reaction was followed by t.l.c. or n.m.r. until no starting material remained (30 m). The products were filtered and the filtrate was concentrated to ca. 10 ml at 14 mmHg and then treated with petrol (70 ml, b.p. 40–60), and allowed to stand for 3 h. The solution was decanted from a dark oil which was produced and quickly washed with ice water (2 × 100 ml), dried and evaporated to give the dichloride. Yield: 80%; $d_H$ 7.6 (2H, d, J Hz), 7.0 (2H, d, J Hz), 6.8 (1H, s), 3.9 (3H, s).

b) 3,4-Dimethoxy(dichloromethyl)benzene

In the same way as described under 12 I a), the tile compound was prepared using a reaction time of 30m, Yield: 79%; $d_H$ 7.05 (1H, br.s), 7.0 (1H, dd, J 8, 2 Hz), 6.7 (1H, d, J 8 Hz), 6.55 (1H, s), 3.85 (3H, s), 3.8 (3H, s).

c) 3,4,5-Trimethoxy(dichloromethyl)benzene

In the same way as described under 12 I a), the tile compound was prepared using a reaction time of 18h, Yield: 100%; (Found M+: 250.0087. $C_{10}H_{12}Cl_2O_3$ requires: 250.0163) showed $d_H$ 6.77 (2H, s), 6.63 (1H, s), 3.86 (6H, s), 3.83 (3H, s); $d_C$ 151.0, 133.5, 101.2, 69.8, 58.6, 54.4.

d) 2,3-Dimethoxy(dichloromethyl)benzene

In the same way as described under 12 I a), the tile compound was prepared using a reaction time of 18h, Yield: 87%; $d_H$ 7.25 (1H, dd, J 2.5, 9 Hz), 7.0 (1H, s), 6.85 (1H, t, J 9 Hz), 6.7 (1H, dd, J 2.5, 9 Hz), 3.8 (3H, s), 3.7 (3H, s).

e) 3,5-Dimethoxy(dichloromethyl)benzene

In the same way as described under 12 I a), the title compound was prepared using a reaction time of 18h, Yield: 100%; $d_H$ 6.6 (2H, d, J 2 Hz), 6.5 (1H, s), 6.3 (1H, t, J 2 Hz), 3.75 (6H, s).

f) 2,4-Dimethoxy(dichloromethyl)benzene

In the same way as described under 12 I a), the title compound was prepared using a reaction time of 18h, Yield: 18%; The compound was very unstable and showed $d_H$ 6.4–7.4 (4H, complex), 3.8 (3H, s), 3.7 (3H, s).

g) 3,4-Methylenedioxy(dichloromethyl)benzene

In the same way as described under 12 I a), the title compound was prepared using a reaction time of 1h, Yield: 100 %; $d_H$ 6.7–7.3 (3H, complex), 6.6 (1H, s), 5.95 (2H, s).

II Preparation of tetramethyloyolopropanes a) 3-Chloro-3-(4-methoxyphenyl)-1,1,2,2,-tetramethylcyclopropane

The dichloride (1 mol. equiv.) in 1,2-dimethoxyethane (60 ml) was added over 30 m to a stirred refluxing suspension of potassium t-butoxide (2 mol.equiv.) in 2,3-dimethylbut-2-ene (3 mol.equiv.). After 18 h, dichloromethane (50 ml) was added and the organic layer was washed with water (3×50 ml) and then 10% hydrochloric acid (50 ml). The aqueous layer was re-extracted with dichloromethane (100 ml), dried and evaporated at 14 mmHg. The products were purified either by recrystallisation or by column chromatography over silica. Yield: 80%; $d_H$ 7.22 (2H, d, 8.6 J Hz), 6.85 (2H, d, J 8.6 Hz), 3.8 (3H, s), 1.35 (6H, s), 1.03 (6H, s).

b) 3-Chloro-3-(3,4-dimethoxyphenyl)-1,1,2,2-tetramethylcyclopropane

In the same way as described under 12 II a), the title compound was prepared in a yield of 82% (Found M+: 268 1250. $C_{15}H_{21}ClO_2$: 268.1230) showed $d_H$ 6.8 (4H, complex), 3.95 (3H, s), 3.9 (3H, s), 1.3 (6H, s), 1.0 (6H, s).

c) 3-Chloro-3-(3,4,5-trimethoxyphenyl)-1,1,2,2-tetramethylcyclopropane

In the same, way as described under 12 II a), the title compound was prepared in a yield of 54 % (Found: C 64.28; H 7.90. $C_{16}H_{23}ClO_3$ requires: C 64.3; H 7.7) which showed $d_H$ 6.5 (1H, s), 3.85 (9H, br.s), 1.37 (6H, s), 1.07 (6H, s); $d_C$ 153.0, 137.6, 135.7, 108.1, 60.85, 60.75, 56.1, 26.7.

d) 3-Chloro-3-(2,3-dimethoxyphenyl)-1,1,2,2-tetramethylcyclopropane

In the same way as described under 12 II a), the title compound was prepared in a yield of 39%, m.p. 123°–125° C. (Found M+: 268.1255. $C_{15}H_{21}ClO_2$ requires: 268.1230) showed $d_H$ 6.7–7.3 (4H, complex), 3.95 (3H, s), 3.83 (3H, s), 1.34 (3H, s), 1.32 (3H, s), 1.06 (3H, s), 0.93 (3H, s).

e) 3-Chloro-3-(3,5-dimethoxyphenyl)-1,1,2,2-tetramethylcyclopropane

In the same way as described undre 12 II a), the title compound was prepared in a yield of 90%, m.p. 119°–121° C. (Found: C, 66.70; H, 7.78. $C_{15}H_{21}ClO_2$ requires: C, 67.0: H, 7.8) which showed $d_H$ 6.42 (2H, d, J 2.3 Hz), 6.37 (1H, t, J 2.3 Hz), 3.79 (6H, s), 1.35 (6H, s), 1.06 (6H, s); $d_C$ 160.6, 142.3, 109.0, 99.6, 55.3, 26.6, 21.2, 20.0.

f) 3-Chloro-3-(2,4-dimethoxyphenyl)-1,1,2,2-tetramethylcyclopropane

In the same way as described under 12 II a), the title compound was prepared in a yield of 14% $d_H$ 6.85 (3H, br.s), 3.95 (6H, s), 1.5 (6H, s), 1.1 (6H, s). The low yield was probably due to the very high reactivity of the dichloride.

g) 3-Chloro-3-(3,4-methylenedioxyphenyl)-1,1,2,2-tetramethylcyclopropane

In the same way as described under 12 II a), the title compound was prepared in a yield of 41%, based on aldehyde,,m.p. 110°–112° C. (Found M+: 252 0928. $C_{14}H_{17}ClO_2$ requires 252.0917) which showed $d_H$ 6.77 (3H, s), 5.93 (2H, s), 1.33 (6H, s), 1.03 (6H, s); $d_C$ 147.45, 134.3, 124.6, 111.3, 108.3, 101.1, 60.8, 25.8, 21.1, 20.0.

III Ring opening reactions a) 3-Chloro-3-(4-methoxyphenyl)-tetramethylcyclopropane (1.0 g) in carbon tetrachloride (30 ml) was stirred with silica (10.0 g). The reaction was followed by n.m.r. until no starting material remained (18–48 h). The silica was filtered and washed with carbon tetrachloride and ether and the combined organic layers were evaporated to give the products. These were purified either by recrystallisation or by column chromatography. Obtained: 6-methoxy-3- isopropyl-2-methylindene (72 %) (Found M+: 202.1338 $C_{14}H_{18}O$ requires: 202.1358) which showed $d_H$ 7.3 (1H, d, J 8.3 Hz), 6.98 (1H, d, J 2.4 Hz), 6.79 (1H, dd, J 2.4, 8.3 Hz),3.81 (3H, s), 3.21 (2H, s), 3.08 (1H, sep, J 7.1 Hz), 2.03 (3H, br.s), 1.30 (6H, d, J 7.1 Hz).

b) 3-Chloro-3-(3,4-dimethoxyphenyl)-tetramethylcyclopropane gave 5,6-dimethoxy-3-isopropyl-2-methylindene (100%, pure by n.m.r.) (Found M+: 232.1423. $C_{15}H_{20}O_2$ requires: 232.1427) which showed $d_H$ 6.99 (1H, s), 6.98 (1H, s), 3.91 (3H, s), 3.87 (3H, s), 3.17 (2H, s), 3.08 (1H, sep, J 7.1 Hz), 2.04 (3H, br,s), 1.32 (6H, d, J 7.1 Hz); $d_C$ 147.7, 146.2, 138.6, 135.5, 135.3, 108.3, 104.4, 65.9, 56.4, 56.3, 42.9, 27.0, 26.7, 21.1, 15.3, 14.3. In some cases, particularly when impure cyclopropane was used, 3-(3,4-dimethoxyphenyl)-2,4-dimethylpenta-1,3- diene was obtained instead of the indene; this was purified by column chromatography and showed $d_H$ 6.65 (3H, br.s), 4.9 (1H, br.s), 4.75 (1H, br.s), 3.7 (6H, s), 1.8 (3H, s), 1.65 (6H, br.s).

c) 3-Chloro-(3,4,5-trimethoxyphenyl)-1,1,2,2-tetramethylcyclopropane gave 3-(3,4,5-trimethoxy-phenyl)-2,4-dimethylbuta-1,3-diene (33%) (Found M+: 262.1589. $C_{16}H_{22}O_3$ requires: 262.1569) which showed $d_H$ 6.39 (2H, s), 5.03 (1H, br.s), 4.84 (1H, br.s), 3.85 (3H, s), 3.83 (6H, s), 1.86 (3H, br.s), 1.68 (3H, br.s), 1.66 (3H, br.s); $d_C$ 152.7, 146.0, 139.1, 136.9, 136.5, 129.0, 128.5, 128.2, 114.2, 106.4, 60.8, 56.0, 22.6, 22.0, 21.8.

d) 3-Chloro-(2,3-dimethoxyphenyl)-1,1,2,2-tetramethyl-cyclopropane gave a complex mixture which did not contain indene. Column chromatography gave (2,3-dimethoxyphenyl)-2,4-dimethyl- penta-1,3-diene (36%) which showed $d_H$ 6.3-7.0 (3H, complex), 4.9 (1H, br.s), 4.75 (1H, br.s), 3.75 (3H, s), 3.6 (3H, s), 1.9 (3H, s), 1.7 (3H, s), 1.5 (3H, s).

e) 3-Chloro-(3,5-dimethoxyphenyl)-1,1,2,2-tetramethyl-cyclopropane gave 3-(3,5-dimethoxy-phenyl)-2,4-dimethyl-penta-1,3-diene (90%) which showed $d_H$ 6.3 (3H, s), 5.0 (1H, m), 4.8 (1H, m), 3.8 (6H, s), 1.9 (3H, s), 1.7 (6H, s).

f) 3-Chloro-(2,4-dimetnoxypnenyl)-1,1,2,2-tetramethyl-cyclopropane gave 4,6-dimethoxy-3-isopropyl-2-methylindene (67%) which showed $d_H$ 6.8 (2H, s), 3.8 (6H, br.s), 3.1 (2H, br.s), 2.9 (1H, sep, J 7 Hz), 2.0 (3H, s), 1.2 (6H, d, J 7 Hz), together with the diene (ratio ca. 3:1); the n.m.r. spectrum of the latter included signals at 4.9 (1H, m), 4.75 (1H, m), 1.8 (3H, s) and 1.5 (6H, br.s).

g) 3-Chloro-(3,4-methylenedioxyphenyl)-1,1,2,2-tetramethylcyclopropane gave 5,6-methylene-dioxy-3-isopropyl-2-methylindene (75 %) m.p.58°-60° C. from methanol (Found M : 216.1 $C_{14}H_{16}O_2$ requires: 216.1150) which showed $d_H$ 6.93 (1H, s), 6.87 (1H, s), 5.9 (2H, s), 3.14 (2H, s), 3.05 (1H, sep, J 7.1 Hz), 2.03 (3H, s), 1.29 (6H, d, J 7.1 Hz); $d_C$ 146.0, 144.4, 141.6, 139.4, 136.5, 135.6, 105.1, 101.2, 100.7, 42.8, 26.7, 21.0, 14.3. The crude product after 18 h reaction contained a small quantity of the corresponding diene by n.m.r. (ratio ca. 6:1); if the reaction was allowed to proceed for 23h the ratio became ca. 12:1.

In view of the above it will be appreciated that in this specification the term allyl compound also includes internally cyclised compounds as the indene derivatives described hereinbefore.

We claim:

1. A process for the production of a diene or allyl product comprising contacting in organic solution with silica a compound of the formula I:

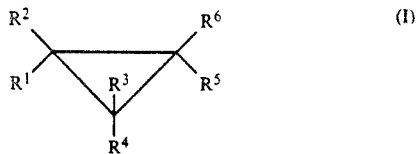

in which $R^1$ is a heteroaryl selected from the group consisting of furyl, thiazyl, pyridyl, and thienyl, or an aryl group where the heteroaryl or aryl groups are optionally substituted by alkoxy, alkyl, halogen, or aryl groups $R^2$ is halogen, $R^3$, $R^4$, $R^5$ and $R^6$ are independently selected from the group consisting of hydrogen, alkyl, aralkyl, aryl, alkenyl, a heteroaryl selected from the group consisting of furyl, thiazyl, pyridyl, and thienyl, provided that at least one of the groups $R^3$, $R^4$, $R^5$ and $R^6$ are other than hydrogen, to open the ring by breaking the bond joining the carbon atom attached to $R^3$ and the carbon atom attached to $R^6$ to produce a diene or allyl product.

2. A process according to claim 1 in which $R^1$ is a heteroaryl group or an aryl group, substituted by one or more $C_{1-4}$-alkoxy groups.

3. A process according to claim 1 in which none of $R^3$ to $R^6$ represent hydrogen.

4. A process according to claim 3 in which each of groups $R^3$ to $R^6$ are independently selected from lower alkyl groups, or two of the groups may together form a lower alpha, omega-alkylene group.

5. A process according to claim 1, in which $R^2$ is bromine or chlorine.

6. A process according to claim 1, in which $R^1$ is 2-or 3-thienyl.

7. A process according to claim 1, in which $R^1$ is phenyl.

8. A process according to claim 1, in which $R^1$ is phenyl substituted with methoxy groups.